United States Patent
Overaker et al.

(10) Patent No.: US 6,743,232 B2
(45) Date of Patent: Jun. 1, 2004

(54) TISSUE SCAFFOLD ANCHOR FOR CARTILAGE REPAIR

(76) Inventors: David W. Overaker, 9 West St., Annandale, NJ (US) 08801; Joseph H. Contiliano, 303 Aldin Rd., Stewartsville, NJ (US) 08886

( * ) Notice: Subject to any disclaimer, the term of this patent is extended or adjusted under 35 U.S.C. 154(b) by 353 days.

(21) Appl. No.: 09/793,693

(22) Filed: Feb. 26, 2001

(65) Prior Publication Data

US 2002/0120274 A1 Aug. 29, 2002

(51) Int. Cl.$^7$ .......................... A61B 17/56; A61B 17/58; A61F 2/30
(52) U.S. Cl. ........................................................ 606/72
(58) Field of Search ............................ 606/72, 151, 53, 606/232; 623/16, 18; A61B 17/56

(56) References Cited

U.S. PATENT DOCUMENTS

| | | |
|---|---|---|
| 3,929,971 A | 12/1975 | Roy |
| 4,045,418 A | 8/1977 | Sinclair |
| 4,057,537 A | 11/1977 | Sinclair |
| 4,105,034 A | 8/1978 | Shalaby et al. |

(List continued on next page.)

FOREIGN PATENT DOCUMENTS

| | | | |
|---|---|---|---|
| EP | 0274898 | | 7/1988 |
| EP | 0278583 | | 8/1988 |
| EP | 0464163 | | 1/1992 |
| EP | 1027897 | | 8/2000 |
| EP | 1129675 | | 9/2001 |
| WO | 9916478 | | 4/1999 |
| WO | 9916479 | | 4/1999 |
| WO | 0020354 | | 4/2000 |
| WO | WO 00/74554 | * | 12/2000 |
| WO | 0074554 | | 12/2000 |

OTHER PUBLICATIONS

A.F. Tencer, et al., "Compressive Properties Of Polymer Coated Synthetic Hydroxyapatite For Bone Grafting", Journal of Biomedical Materials Research, vol. 19, John Wiley & Sons, Inc., (1985), pp. 957–969.

Ainslie T. Young, "Microcellular Foams via Phase Separation" J. Vac. Sci. Technol. A 4 (3), American Vacuum Society, May/Jun. (1986), pp. 1128–1133.

Daniel Cohn, et al., "Biodegradable PEO/PLA Block Copolymers" Journal of Biomedical Materials Research, vol. 22, John Wiley & Sons, Inc., (1988), pp. 993–1009.

Allcock, "Polyphosphazenes", Encyclopedia of Polymer Science and Engineering, vol. 13, John Wiley & Sons, Inc., New York (1988), pp. 31–41.

D. Cohn, "New Tailor–Made Biodegradable Polymeric Biomaterials" Polymer Preprints, vol. 30, No. 1, Division of Polymer Chemistry, Inc., Dallas, Texas, (Apr. 1989), p. 498.

Shigenobu Matsuda, "Thermodynamics of Formations of Porous Polymeric Membrane from Solutions", Polymer Journal, vol. 23, No. 5, (1991), pp. 435–444.

Jorge Heller, "Poly(ortho esters)", Handbook Of Biodegradable Polymers, Harwood Academic Publishers, Netherlands, (1997), pp. 99–118.

(List continued on next page.)

*Primary Examiner*—Henry Bennett
*Assistant Examiner*—Sabrina Dagostino

(57) ABSTRACT

A device for attaching a tissue replacement scaffold to a bone has a platform positionable in substantially parallel relationship to the bone for retaining the tissue scaffold proximate to the bone. A post extends from the platform and is insertable into a hole formed in the bone. One or more ribs extend from a side surface of the post along a portion of its length. The ribs have an increasing cross-sectional area to establish an increasing interference fit relative to the hole in the bone tissue. The ribs have a sharp edge that grips the sides of the hole in the bone such that the ribs restrict rotation or withdrawal of the device.

18 Claims, 4 Drawing Sheets

U.S. PATENT DOCUMENTS

| | | |
|---|---|---|
| 4,130,639 A | 12/1978 | Shalaby et al. |
| 4,140,678 A | 2/1979 | Shalaby et al. |
| 4,141,087 A | 2/1979 | Shalaby et al. |
| 4,186,448 A | 2/1980 | Brekke |
| 4,205,399 A | 6/1980 | Shalaby et al. |
| 4,208,511 A | 6/1980 | Shalaby et al. |
| 4,861,733 A | 8/1989 | White |
| 5,067,964 A | 11/1991 | Richmond et al. |
| 5,084,051 A | 1/1992 | Tormala et al. |
| 5,133,755 A | 7/1992 | Brekke |
| 5,306,311 A | 4/1994 | Stone et al. |
| 5,314,478 A | 5/1994 | Oka et al. |
| 5,314,989 A | 5/1994 | Kennedy et al. |
| 5,403,347 A | 4/1995 | Roby et al. |
| 5,431,679 A | 7/1995 | Bennett et al. |
| 5,458,643 A | 10/1995 | Oka et al. |
| 5,464,929 A | 11/1995 | Bezwada et al. |
| 5,468,253 A | 11/1995 | Bezwada et al. |
| 5,486,359 A | 1/1996 | Caplan et al. |
| 5,502,159 A | 3/1996 | Liu et al. |
| 5,514,378 A | 5/1996 | Mikos et al. |
| 5,522,895 A | 6/1996 | Mikos |
| 5,595,751 A | 1/1997 | Bezwada et al. |
| 5,597,579 A | 1/1997 | Bezwada et al. |
| 5,607,474 A | 3/1997 | Athanasiou et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,624,463 A | 4/1997 | Stone et al. |
| 5,632,745 A | 5/1997 | Schwartz |
| 5,645,850 A | 7/1997 | Bezwada et al. |
| 5,648,088 A | 7/1997 | Bezwada et al. |
| 5,677,355 A | 10/1997 | Shalaby et al. |
| 5,686,091 A | 11/1997 | Leong et al. |
| 5,698,213 A | 12/1997 | Jamiolkowski et al. |
| 5,700,583 A | 12/1997 | Jamiolkowski et al. |
| 5,711,960 A | 1/1998 | Shikinami |
| 5,713,374 A | 2/1998 | Pachence et al. |
| 5,716,413 A | 2/1998 | Walter et al. |
| 5,749,874 A | 5/1998 | Schwartz |
| 5,755,792 A | 5/1998 | Brekke |
| 5,769,899 A | 6/1998 | Schwartz et al. |
| 5,770,193 A | 6/1998 | Vacanti et al. |
| 5,770,417 A | 6/1998 | Vacanti et al. |
| 5,859,150 A | 1/1999 | Jamiolkowski et al. |
| 5,984,927 A | 11/1999 | Wenstrom, Jr. et al. |
| 6,103,255 A | 8/2000 | Levene et al. |
| 6,209,178 B1 | 4/2001 | Wiese et al. |
| 6,251,143 B1 | 6/2001 | Schwartz et al. |
| 6,355,066 B1 | 3/2002 | Kim |
| 6,371,958 B1 * | 4/2002 | Overaker .................... 606/72 |

OTHER PUBLICATIONS

J. Vandorpe, et al., "Biodegradable Polyphosphazenes For Biomedical Applications", Handbook Of Biodegradable Polymers, Harwood Academic Publishers, Netherlands, (1997), pp. 161–182.

John Kemnitzer, et al., "Degradable Polymers Derived From the Amino Acid L-Tyrosine", Handbook Of Biodegradable Polymers, Harwood Academic Publishers, Netherlands, (1997), pp. 251–272.

B. Kreklau, et al., "Tissue Engineering of Biphasic Joint Cartilage Transplants", Biomaterials 20, Elsevier Science Ltd., (1999), pp. 1743–1749.

Gabriele G. Niederauer, et al., "Evaluation of Multiphase Implants for Repair of Focal Osteochondral Defects in Goats", Biomaterials 21, Elsevier Science Ltd., (2000), pp. 2561–2574.

D. Schaefer, et al., "In Vitro Generation of Osteochondral Composites", Biomaterials 20, Elsevier Science Ltd., (2000), pp. 2599–2606.

Vicki Rosen, Ph.D, et al., "Chapter 1—Introduction and Goat", The Cellular and Molecular Basis of Bone Formation and Repair, R.G. Landes Company, Austin, Texas, (1995), pp. 1–41.

* cited by examiner

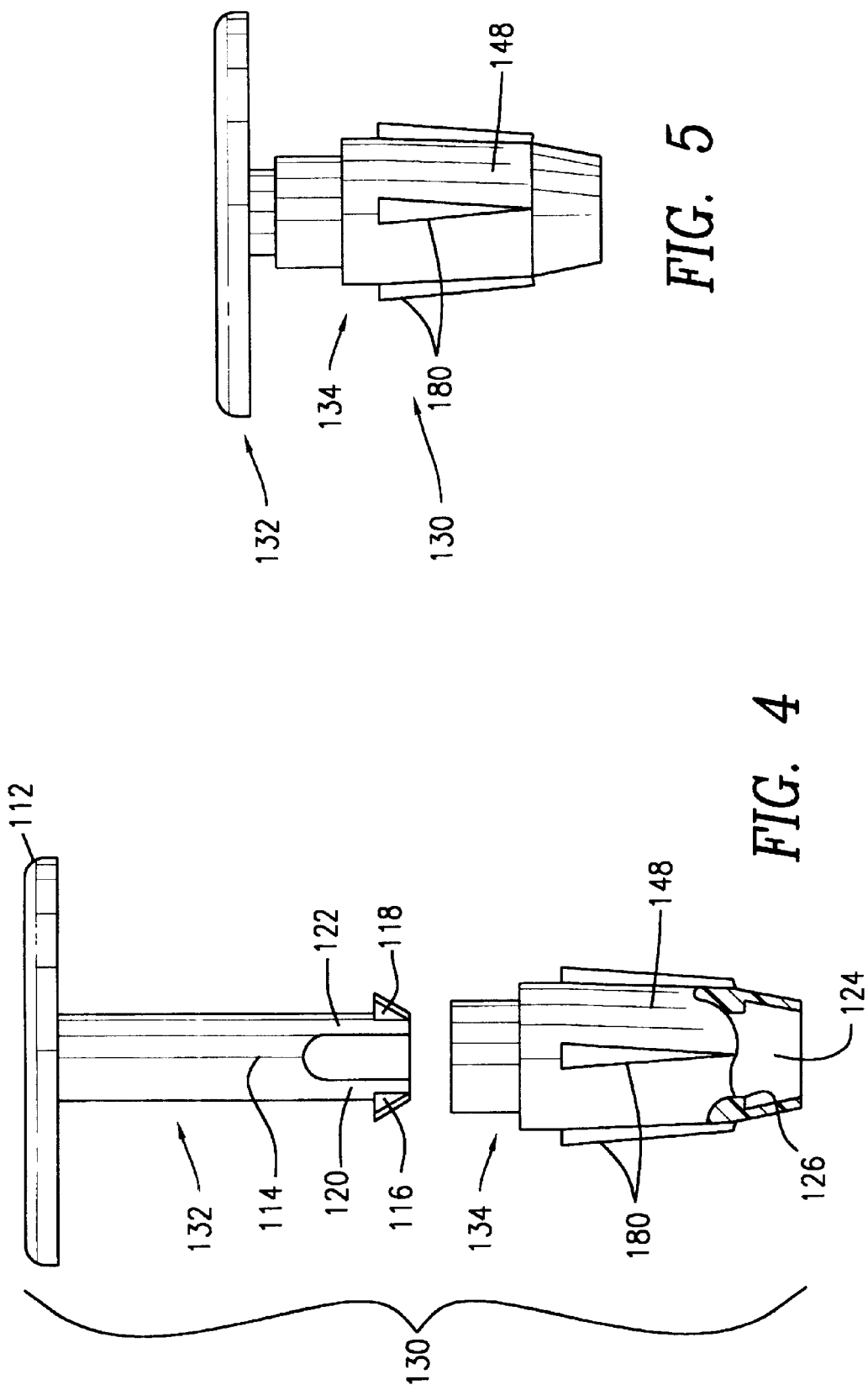

US 6,743,232 B2

TISSUE SCAFFOLD ANCHOR FOR CARTILAGE REPAIR

FIELD OF THE INVENTION

The present invention relates to scaffold fixation devices useful in articular cartilage repair and more specifically to a device for fastening an articular cartilage scaffold to underlying bone.

BACKGROUND OF THE INVENTION

Articular cartilage is a tissue that covers the articulating surfaces between bones in joints, such as the knee or elbow, which is subject to catastrophic or repetitive stress injury. Various means have been proposed to address such injuries including repair via tissue engineering. Tissue engineering is defined as the application of engineering disciplines to either maintain existing tissue structures or to enable new tissue growth. This engineering approach generally includes the delivery of a tissue scaffold that serves as an architectural support onto which cells may attach, proliferate, and synthesize new tissue to repair a wound or defect. Surgical use of a tissue scaffold requires a fixation means to secure the scaffold to the bone beneath the wounded cartilage site. Secure fixation of the scaffold within the wound site is necessary for proper healing.

Frequently, scaffolds, prostheses and fasteners used in orthopedic applications are made from synthetic absorbable biocompatible polymers which are well known in the art. Such polymers typically are used to manufacture medical devices which are implanted in body tissue and absorb over time. Synthetic, absorbable, biocompatible aliphatic polyesters include homopolymers, copolymers (random, block, segmented and graft) of monomers such as glycolic acid, glycolide, lactic acid, lactide(d, I, meso and mixtures thereof), ε-caprolactone, trimethylene carbonate and p-dioxanone. Numerous U.S. Patents describe these polymers, including U.S. Pat. Nos. 5,431,679; 5,403,347; 5,314,989; and 5,502,159. Devices made of an absorbable material have the advantage that they are absorbed by the body after healing has occurred.

U.S. Pat. No. 5,067,964 describes an articular cartilage repair piece which includes a backing layer of non-woven, feted fibrous material which is either uncoated or covered by a coating of tough, pliable material. A number of means are disclosed for fastening the repair piece to the underlying bone. U.S. Pat. Nos. 5,306,311 and 5,624,463 describe a prosthetic, resorbable articular cartilage and methods of its fabrication and insertion. U.S. Pat. No. 5,713,374 describes an attachment method to hold a biomaterial in place until healing occurs. U.S. Pat. Nos. 5,632,745 and 5,749,874 and 5,769,899 describe a bioabsorbable cartilage repair system.

Articular joint loading is very complex, involving high compressive loads combined with high shear loads associated with sliding articulation of the opposing surfaces. A device implanted into the articular joint space must have sufficient strength to withstand these loads. Particularly important is that the device should be fixed in the underlying bone so that it cannot rotate or separate from the bone under the action of high shear loads in the joint space. U.S. Pat. No. 5,749,874 teaches that if vascular invasion and cellular migration is to be effected between the healthy tissue and the scaffold, means must be provided to preclude rotation of the scaffold relative to the fixation device, but does not describe a means of keeping the fixation device itself from rotating in relation to the surrounding tissues or from pulling out.

Accordingly, it would be advantageous to provide a scaffold fixation device which has a fixation means that engages the bone to prevent rotation and separation.

SUMMARY OF THE INVENTION

The limitations of prior art devices for attaching a tissue scaffold to bone tissue are overcome by the present invention which includes an attachment device having a platform positionable in substantially parallel relationship to the bone tissue for retaining the tissue scaffold proximate to the bone tissue. A post extends from the platform and is insertable into a hole formed in the bone tissue. At least one rib extends from a surface of the post along a portion of its length from a first point distal to the platform to a second point intermediate the first point and the platform. The rib has a cross-sectional area that increases along the length of the rib in the direction from the first point to the second point and establishes an interference fit relative to the hole in the bone tissue to prevent rotation of the device relative to the bone tissue.

BRIEF DESCRIPTION OF THE FIGURES

FIG. 4 is an exploded view of a second exemplary embodiment of the present invention;

FIG. 5 is a side elevation view of the device of FIG. 4, assembled; and

DETAILED DESCRIPTION OF THE INVENTION

Figure 1:
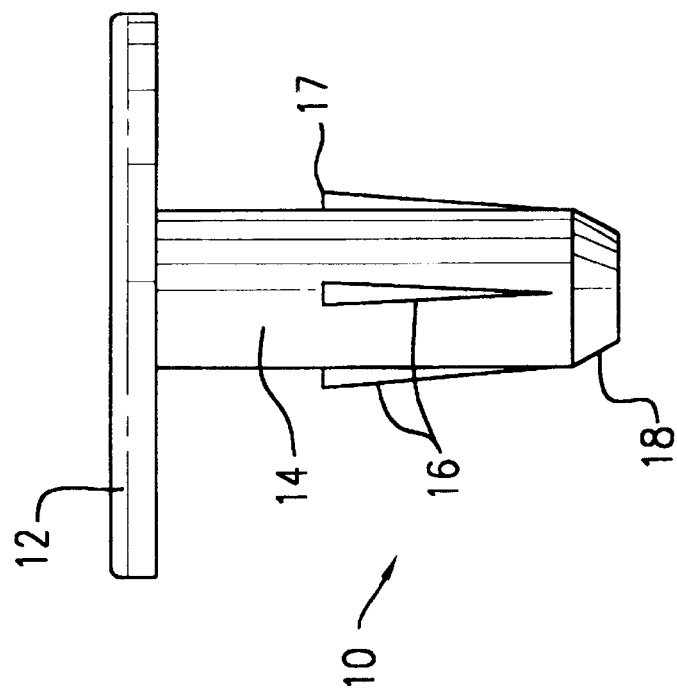
FIG. 1 is a side elevation view of a scaffold fixation device in accordance with an exemplary embodiment of the present invention.

FIG. 1 shows a scaffold fixation device 10 for fastening an articular cartilage scaffold to underlying bone. The device 10 has a scaffold attachment platform 12 with a post 14 extending therefrom at approximately 90°. Depending upon the application, this angular relationship may be varied. Vertical ribs 16 extend along a portion of the length of the post 14 and taper downwards in width and height as they extend from edge 17 to chamfered distal tip 18. The taper of vertical ribs 16 enhances the ability of the vertical ribs 16 to gradually cut into surrounding bone during insertion of scaffold fixation device 10 into an appropriately sized hole in a bone to which the device 10 is attached. While the ribs 16 shown are in the form of a longitudinally bisected, elongated cone, other tapering shapes could be employed, such as an elongated wedge with or without a knife-edge bevel.

Figure 2:
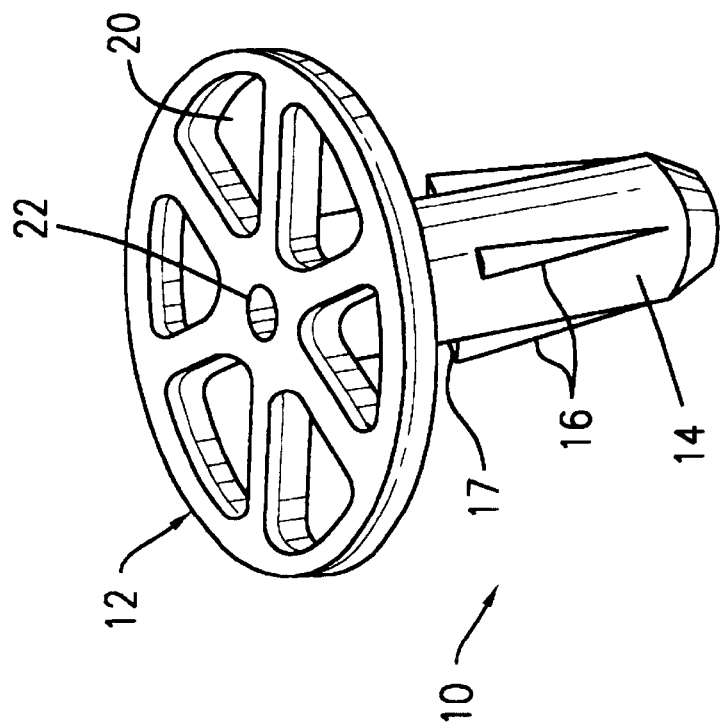
FIG. 2 is a perspective view of the device of FIG. 1.

FIG. 2 shows a perspective view of scaffold fixation device 10 showing perforations 20 in disk-shaped platform 12 that allow fluid and cells to travel to and from the scaffold promoting cell proliferation and ingrowth. While six triangular perforations 20 are shown in FIG. 2, the perforations 20 can be any number, size or shape, e.g., circular or trapezoidal and accordingly are not limited to the shape or arrangement shown in the figures. A guide wire channel 22 extends longitudinally through fixation device 10 along the axis of post 14. As is known in the art, a guide wire may be utilized to assist in placing the device 10, viz, by inserting an end of a guide wire into a hole bored in a bone and then threading the device 10 over the guide wire, i.e., via channel 22, such that the post 14 enters the hole in the bone (See FIG. 3).

Figure 3:
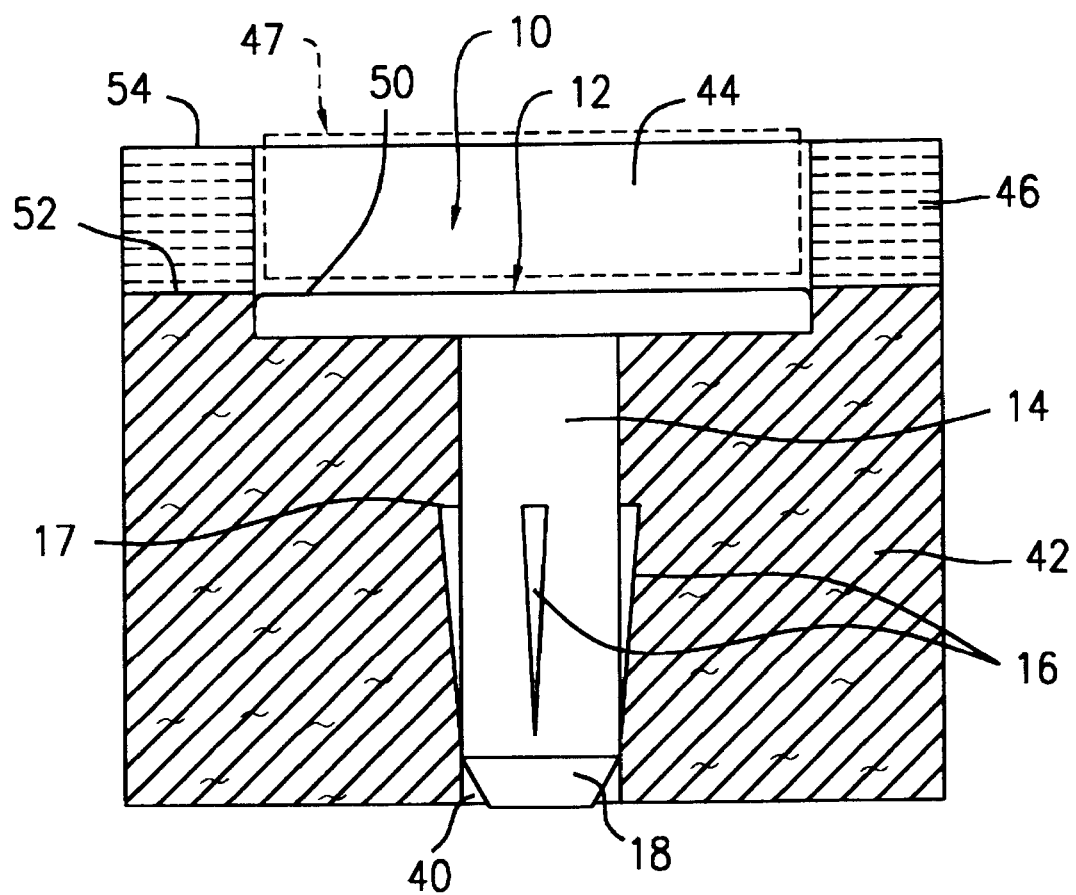
FIG. 3 is a side elevation view of the device of FIG. 1 deployed in bone.

FIG. 3 shows a side elevation view of scaffold fixation device 10 which has been surgically positioned within a hole 40 drilled in bone tissue 42. The diameter of the hole 40 is selected such that an interference fit is made between the hole 40 and post 14 with vertical ribs 16. That is, hole 40 has diameter which is less than the outermost diameter of vertical ribs 16. Preferably, hole 40 has a diameter that is the same as or slightly smaller than the outermost diameter (root diameter) of post 14 (not including ribs 16). The scaffold fixation device 10 is preferably fabricated from a material that is sufficiently unyielding such that post 14 and vertical ribs 16 have sufficient radial stiffness and strength to cause the vertical ribs 16 to cut into the bone tissue 42 surrounding the hole 40. This intrusion into the bone 42 has the effect of rotationally fixing the scaffold fixation device 10 to the bone tissue 42. In addition, axial fixation of the device 10 is achieved by vertical ribs 16, the sharp edges 17 of which engage trabecular bone tissue 42 when subjected to an axial force which would otherwise pull the scaffold fixation device 10 out of the hole 40 in the bone 42. A hole 44 is drilled in cartilage tissue 46 with a diameter at least as large as the outermost diameter of platform 12 to accommodate the platform 12 therein in a position permitting the scaffold 47 (shown diagrammatically in dotted lines and displaced slightly) to be attached to the device 10 by sutures or adhesives, in a known manner. The depths of hole 40 in the bone and the hole 44 in the cartilage are selected such that, when post 14 is inserted completely into hole 40, upper surface 50 of platform 12 is in alignment with or slightly below upper surface 52 of the bone tissue 42, i.e., the platform 12 may be countersunk into the bone 42. The scaffold 47 is accommodated within hole 44 in the cartilage (between platform 12 and upper cartilage surface 54). Post 14 may also have a chamfered lower edge 18 which aids in guiding post 14 into the hole 40 in the bone tissue 42. As noted above, a surgical guide wire may be passed through guide wire channel 22 during surgery to align scaffold fixation device 10 with bone hole 40. The fixation device 10 may be made from a non-porous material or from materials that are partially or wholly porous to allow cell invasion into the device.

Figure 6:
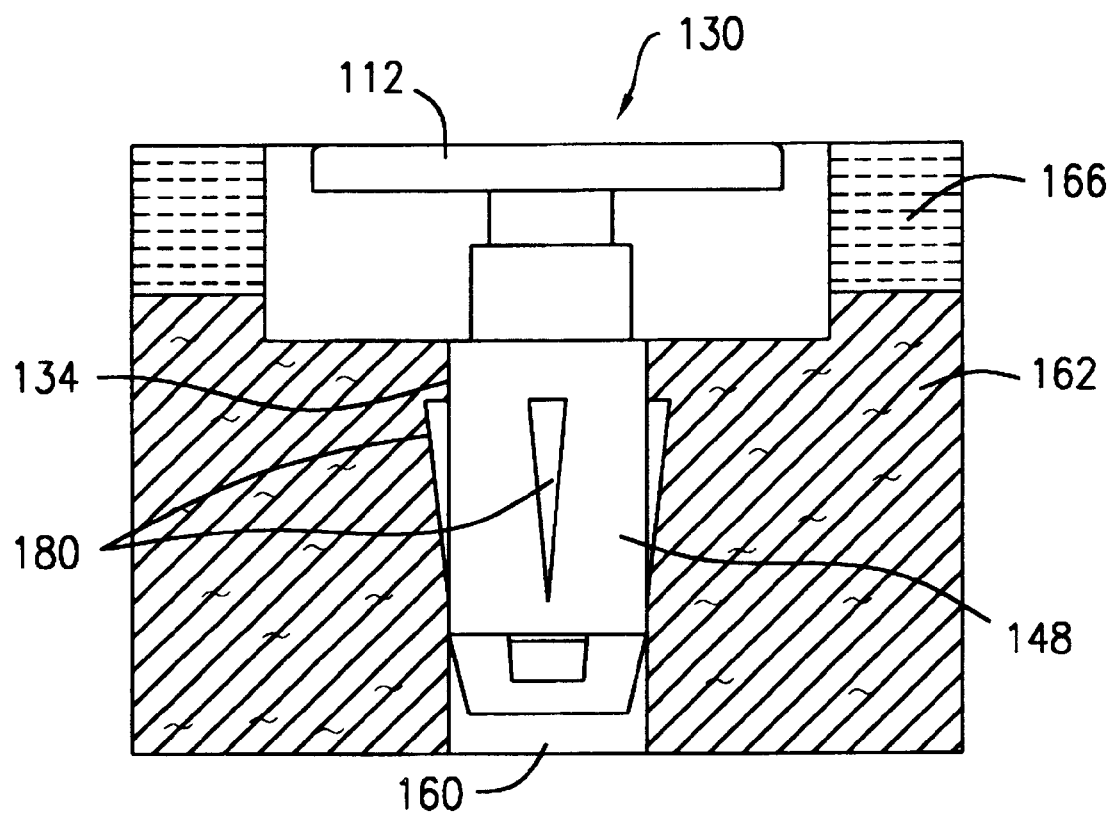
FIG. 6 is a side elevation view of the device of FIG. 4 deployed in bone.

A two-piece embodiment of the invention is shown in FIGS. 4 through 6, which show a two-piece scaffold fixation device 130 similar to a device described in the copending patent application entitled, "Scaffold Fixation Device for Use in Articular Cartilage Repair", U.S. application Ser. No. 09/517,602 filed Mar. 2, 2000 and assigned to Ethicon, Inc., hereby incorporated herein by reference, FIGS. 14 through 20 and the associated description thereof being particularly relevant in describing the interlocking relationship displayed by a two-piece scaffold fixation device.

FIG. 4 shows a two-piece scaffold fixation device 130 with top component 132 and fixation component 134. The top component 132 has a scaffold attachment platform 112 from which extends a coupling pin 114 with a pair of latches 116, 118 projecting from corresponding resilient arms 120, 122. The coupling pin 114 telescopes into a mating axial bore 124 in the fixation component 134, with the latches 116, 118 clipping over an internal ledge 126 when the pin 114 is pressed fully home into the bore 124. The fixation component 134 has vertical anchoring ribs 180 having a similar form and function as the vertical ribs 16 shown in FIGS. 1–3. The ribs 180 are disposed about the outer peripheral surface of cylindrically shaped anchor section 148 of the fixation component 134. FIG. 5 shows the scaffold fixation device 130 with the top component 132 and fixation component 134 assembled.

FIG. 6 shows scaffold fixation device 130 after having been surgically inserted in bone tissue 162, showing the vertical anchoring ribs 180 embedded in the bone tissue 162 surrounding hole 160 to prevent rotation of fixation component 134 within the hole 160. The device 130 would be utilized for attaching a scaffold (see FIG. 3) to a bone 162 by boring a suitable hole 160 in the bone 162. The fixation component 134 is inserted into the hole 160 and driven home. The coupling pin 114 of the top component 132 can then be inserted into bore 124 of the fixation component and pressed in until the latches 116, 118 latch over ledge 126 (See FIG. 4).

Although FIGS. 1–6 show a certain number and shape of vertical ribs 16 and vertical anchoring ribs 180, those skilled in the mechanical arts will appreciate that various numbers and shapes of ribs 16, 180 protruding from post 14 or anchor section 148 will create a noncircular cross-section along at least a portion of post 14 or anchor section 148 and result in rotational and axial fixation in bone. Fixation device 130 may be either solid or partially or wholly porous to allow cell invasion into the device.

Suitable materials from which the scaffold fixation device 10, 130 may be formed include biocompatible polymers such as aliphatic polyesters, polyorthoesters, polyanhydrides, polycarbonates, polyurethanes, polyamides and polyalkylene oxides. The present invention also can be formed from absorbable polymers, glasses or ceramics comprising calcium phosphates and other biocompatible metal oxides (i.e., CaO), metals, combinations of metals, autograft, allograft, or xenograft bone tissues.

In the preferred embodiment, the scaffold fixation device 10, 130 is formed from aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, $\epsilon$-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyldioxepan-2-one, 6,8-dioxabicycloctane-7-one and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

In another embodiment of the present invention, the polymers and blends from which it is formed can be used as a therapeutic agent release matrix. Prior to forming the device 10, 130, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors, including bone morphogenic proteins (i.e. BMP's 1–7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β I–III), vascular endothelial growth factor (VEGF); and other naturally derived or genetically engineered proteins, polysaccharides, glycoproteins, or lipoproteins. The foregoing growth factors are known to those with skill in the art and described in *The Cellular and Molecular Basis of Bone Formation and Repair* by Vicki Rosen and R. Scott Thies, published by R. G. Landes Company hereby incorporated herein by reference.

Matrix materials for the present invention may be formulated by mixing one or more therapeutic agents with the polymer. Alternatively, a therapeutic agent could be coated on to the polymer, preferably with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

We claim:

1. A device for attaching a tissue scaffold to bone tissue, comprising:

a platform positionable in substantially parallel relationship to the bone tissue for retaining the tissue scaffold proximate to the bone tissue;

a post extending from the platform, said post being insertable into a hole formed in the bone tissue; and at least one rib extending from a surface of said post along a portion of the length of said post from a first point distal to said platform to a second point intermediate said first point and said platform, said at least one rib having a cross-sectional area that increases along the length of said rib in the direction from said first point to said second point, said at least one rib establishing an interference fit relative to the hole in the bone tissue to prevent rotation of said device relative to the bone tissue, said at least one rib being shorter in length than the depth of the hole in the bone tissue and having a diverging surface which expands in width in the direction from said first point to said second point and which diverges from the surface of said post in the direction from said first point to said second point, and said at least one rib terminating proximate said second point in a sharp edge which is positionable within said hole for gripping the bone tissue to resist withdrawal of said device from the hole.

2. The device of claim 1, wherein said at least one rib has a shape approximating a portion of an elongated cone.

3. The device of claim 2, wherein said at least one rib is a plurality of ribs disposed about the outer peripheral surface of said post.

4. The device of claim 3, wherein said post has a chamfered end to aid in the introduction of said post into the hole in the bone tissue.

5. The device of claim 4, wherein said device has a guide wire hole extending axially there through to permit said device to be slipped over a guide wire having one end thereof positioned in the hole for guiding said device into the hole.

6. The device of claim 1, wherein said post extends from said platform at about 90 degrees.

7. The device of claim 1, wherein said platform has a perforation therein to allow fluid and cell transmission through said perforation.

8. The device of claim 1, wherein said device is formed from a material selected from the group consisting of biocompatible polymers, absorbable polymers, glasses, ceramics, metal oxides, bone tissue and therapeutic agents, alone or in combination.

9. A device for attaching a tissue scaffold to bone tissue, comprising:

a platform positionable in substantially parallel relationship to the bone tissue for retaining the tissue scaffold proximate to the bone tissue;

a post extending from the platform and being monolithically formed therewith, said post insertable into a hole formed in the bone tissue;

at least one rib extending from a surface of said post along a portion of the length of said post from a first point distal to said platform to a second point intermediate said first point and said platform, said at least one rib having a cross-section area that increases along the length of said rib in the direction from said first point to said second point, said at least one rib establishing an interference fit relative to the hole in the bone tissue to prevent rotation of said device relative to the bone tissue.

10. A device for attaching a tissue scaffold to bone tissue, comprising:

a platform positionable in substantially parallel relationship to the bone tissue for retaining the tissue scaffold proximate to the bone tissue;

a post extending from the platform, said post being insertable into a hole formed in the bone tissue and being formed independently of said platform; and at least one rib extending from a surface of said post along a portion of the length of said post from a first point distal to said platform to a second point intermediate said first point and said platform, said at least one rib having a cross-section area that increases along the length of said rib in the direction from said first point to said second point, said at least one rib establishing an interference fit relative to the hole in the bone tissue to prevent rotation of said device relative to the bone tissue.

11. The device of claim 10, wherein said platform has a coupling pin extending from a surface thereof, said post having a hollow therein for matingly receiving said coupling pin to couple said platform and said post.

12. The device of claim 11, further including a latch resiliently mounted on said coupling pin, said latch having a locking position and a withdrawn position, said latch permitting said coupling pin to be inserted into said hollow in said post in a coupling relationship with said post when in said withdrawn position and retaining said coupling pin coupled to said post in said locking position.

13. A device for attaching a tissue scaffold to bone tissue, comprising:

attaching means for attaching the scaffold to said device; and retaining means coupled to said attaching means being for retaining said attaching means in proximity to the bone tissue, said retaining means being insertable into a hole formed in the bone tissue and including gripping means extending from the outer periphery thereof for gripping the bone tissue proximate the hole to restrain said device from rotating or pulling away from the bone tissue, said gripping means having an outer surface diverging from said retaining means and expanding in surface area in the direction proximal to said attaching means.

14. The device of claim 13, wherein said gripping means have a gradually increasing interference fit relative to the hole in the bone tissue.

15. The device of claim 14, wherein said gripping means are fully insertable within the hole in the bone tissue and have a sharp edge which gouges into the bone tissue proximate the hole.

16. The device of claim 15, wherein said attaching means has apertures therein for allowing the flow of fluids and cells there through.

17. The device of claim 16, further including coupling means for coupling said attaching means and said retaining means.

18. The device of claim 16, wherein said attaching means and said retaining means are formed from a composition with a porosity permitting ingrowth of cells.

* * * * *